United States Patent [19]

Canevet et al.

[11] Patent Number: 5,134,891
[45] Date of Patent: Aug. 4, 1992

[54] DEVICE TO DETERMINE THE COEFFICIENT OF THE HYDRIC EXPANSION OF THE ELEMENTS OF A COMPOSITE STRUCTURE

[75] Inventors: Maurice Canevet, Rueil-Malmaison; Pascal Lesage, La Queue Lez Yvelines, both of France

[73] Assignee: AEROSPATIALE Societe Nationale Industrielle, Paris, France

[21] Appl. No.: 603,458

[22] Filed: Oct. 25, 1990

[30] Foreign Application Priority Data

Oct. 30, 1989 [FR] France .................... 89 14212

[51] Int. Cl.$^5$ .................................. G01N 33/36
[52] U.S. Cl. ......................... 73/866; 73/865.6
[58] Field of Search ............ 73/760, 866, 865.6, 73/865.5; 33/783, 787–790, 501.02

[56] References Cited

U.S. PATENT DOCUMENTS

| | | | |
|---|---|---|---|
| 3,817,109 | 6/1974 | Audet et al. | 73/865.6 |
| 4,750,374 | 6/1988 | Goss | 73/866 |
| 4,848,161 | 7/1989 | van der Kuur | 73/760 |

OTHER PUBLICATIONS

Gardner, Instrumentation for Environmental Chambers, Electro-Technology, Sep. 1963.
F. E. Grace, et al.; "Environmental Dimensional Monitoring"; IBM Technical Disclosure Bulletin; vol. 9, No. 6, Nov. 1966 p. 689.
R. D. Sandison, et al.; "High-Temperature Dilatometer System for Measuring the Shrinkage Kinetics of a Liquid-Containing Ceramic System"; Rev. Sci. Instrum. vol. 50, No. 1 Jan. 1979; pp. 129 and 130.
C. R. Stroope, et al.; "Electronic Dilatomer"; N.T.I.S. Technical Notes; Jul. 1984, No. 7, Part H; p. 507.

Primary Examiner—Robert Raevis

[57] ABSTRACT

So as to determine the coefficient of hydric expansion $\beta$ of the elements of a composite structure, a sample of this structure is placed in a rigid cradle (10) so that one extremity of the sample is rigidly maintained and that the length variations of the sample are measured by a displacement transducer (12) borne by the cradle. The transducer (12) is preferably a linear differential transformer contact transducer and it is kept under constant humidity by injecting dry air through a flexible tube (60, 64) connected to its rear section. By placing the cradle (10) bearing the sample in a climatic chamber (40), whose humidity is made to vary at a constant temperature, and by at the same time measuring the weight of the sample, it is possible to determine the coefficient $\beta$.

6 Claims, 3 Drawing Sheets

DEVICE TO DETERMINE THE COEFFICIENT OF THE HYDRIC EXPANSION OF THE ELEMENTS OF A COMPOSITE STRUCTURE

FIELD OF THE INVENTION

The invention concerns a device for determining the coefficient of the hydric expansion of a composite structure from samples of this structure which may appear in the form of a tubular bar, a plate or a honeycombed sandwich.

BACKGROUND OF THE INVENTION

The coefficient of the hydric expansion of a composite structure, usually denoted by $\beta$, is determined by the equation:

$$\frac{\Delta}{L_o} = \beta \frac{\Delta M}{M_o}$$

where $L_O$ and $M_O$ respectively represent the initial length and initial weight of a dry sample of the composite structure, $\Delta L$ and $\Delta M$ representing the evolution of these quantities when this sample is impregnated with water.

Knowledge of the coefficient of the hydric expansion $\beta$ is of special interest in space applications, having regard to the fact that the embarked optics are frequently supported by composite structures. In fact, the space vacuum has the effect of draining these composite structures and the release of the water intially contained in these structures is expressed by dimensional variations which are recovered on the optics they support.

Currently, these dimensional variations are taken into account by electro-mechanical devices associated with the embarked optics and which make it possible to correct the positioning of the latter by displacements along the optical axis. However, control of the entire bearer structure and determination of the adjustment sizes of the optics immediately before launching requires a full knowledge of the reaction of the materials when diffused in water.

Furthermore, given the fact that the dimensional variations resulting from the draining under vacuum of an initially humid composite structure are extremely small (sometimes less than 1 $\mu$m per mm of sample) and slow (several weeks), there currently exists no sufficiently accurate and stable dilatometer able to measure these variations to be taken into account during the lifetime of the composite parts supporting the embarked optics.

The installing of such a device has up until now come up against difficulties mainly linked to the fact that existing displacement transducers, which seemed sufficiently accurate and stable so as to be able to be used, were sensitive to the evolution of the ambient humidity in proportions equal to at least the proportions of the measurements to be made.

If it appeared to be possible to resolve this problem by placing the transducer outside the zone containing the sample and in which the ambient humidity is made to vary, this would result in other errors on account of the ensuing need to place a linking member between the transducer and the sample. In fact, this linking member would have traversed a transition zone subjected to the original thermic stresses necessarily resulting in non-compensated deformations and local test environment disturbances.

SUMMARY OF THE INVENTION

The object of the invention is to provide a device making it possible to determine the coefficient of the hydric expansion of a composite material by means of an accurate measurement, this material being stable and insensitive to the surrounding humidity, and to determine the length variations of a sample of this material brought about by the variations of the humidity it contains, which makes it possible to take into account the deformations resulting from evacuating the water in the space vacuum on composite structures supporting the embarked optics and accordingly allows for a significant increase of the precision of these optics, as well as a lightening of the active readjustment systems.

According to the invention, this result is obtained by means of a device making it possible to determine the coefficient of the hydric expansion $\beta$ of the elements of a composite structure, wherein it includes:

a rigid cradle made of a thermically stable material and including means to keep a sample of said structure in a desired position and means to immobilize a first extremity of the sample;

a displacement transducer mounted on the rigid cradle opposite a second extremity of the sample opposing the first one so as to measure the length variations of the sample;

a tune for admitting dry air into the transducer and connected to a dry air source and whose extremity opposite said source overlaps one rear section of the displacement transducer;

a climatic chamber for receiving the rigid cradle and its displacement transducer and able to vary the humidity of the atmosphere encompassing the cradle and the transducer within a determined range; and means for measuring the weight variation of the sample.

By means of a device embodied as above, it is possible to calculate the coefficient of the hydric expansion $\beta$ from of the length and weight measurements by applying the equation (1).

In this device, it is important to note that the injection of dry air into the displacement transducer makes it possible to avoid any drift of the latter according to the ambient humidity, which guarantees accuracy of the measurements, especially when a linear differential transformer detection sensor is used comprising a contact finger axially guided by a rolling bearing whose stability and sensitivity are moreover excellent.

Given the fact that the extremities of the sample may deform inhomogeneously under the effect of the variation of the amount of water contained in this sample, the device has been designed in such a way as to subsequently be freed from these edge effects. To this effect, the means to immobilize the first extremity of the sample are clamping means taking support on lateral faces of the sample, and the contact finger of the transducer is adapted to come into contact with an intermediate member clamped onto the lateral faces of the sample close to the second extremity of said sample.

The displacement transducer is electrically connected to an electric power device which also needs to be placed in a chamber at a constant temperature so as to avoid adversely affecting the accuracy of the measurement. For the same reason, this electric power device is advantageously connected to the mains supply through a d.c.-a.c. converter stabilizing the voltage.

BRIEF DESCRIPTION OF THE DRAWINGS

There now follows a description of a preferred embodiment of the invention, given by way of non-restrictive example, with reference to the accompanying drawings in which:

FIGS. 2 and 3 are cutaway views showing how the rigid cradle of FIG. 1 may also be used to test the samples of composite structures respectively appearing in the form of a honeycombed structure and a flat plate.

DETAILED DESCRIPTION OF THE PREFERRED EMBODIMENTS

According to the invention, samples of the main types of materials used in space and especially for supporting embarked optics are tested on the ground so as to be able to give these structures dimensions which take into account the dimensional variations induced by the release of the water initially contained in these structures when the latter are in a space vacuum.

In order to do this, a device is installed making it possible to determine the coefficient of the hydric expansion $\beta$ of such composite structures from samples having the usual shapes of these structures, that is tubular bars, honeycombed structures and flat plates.

Advantageously, this device shall be used to determine the coefficients $\beta 0$ and $\beta 90$ of samples of composite structures formed of fibers respectively orientated along the longitudinal axis of the sample and perpendicular to this axis. On the basis of the measurements carried out, it is in fact possible to anticipate by means of the calculation the behaviour of the structures formed of fibers orientated along any direction with respect to their longitudinal axis.

The device of the invention firstly includes an extremely accurate time-stable dilatometer designed to be insensitive to variations of the ambient humidity. These properties are essential for using an exploitable measurement, it being observed that the dimensional variations to be measured are often less than 1 $\mu$m per mm of sample, that it needs several weeks for the sample to reach its state of equilibrium, and that the most accurate displacement transducers generally drift by several $\mu$ms when the ambient humidity is made to vary.

Figure 1:
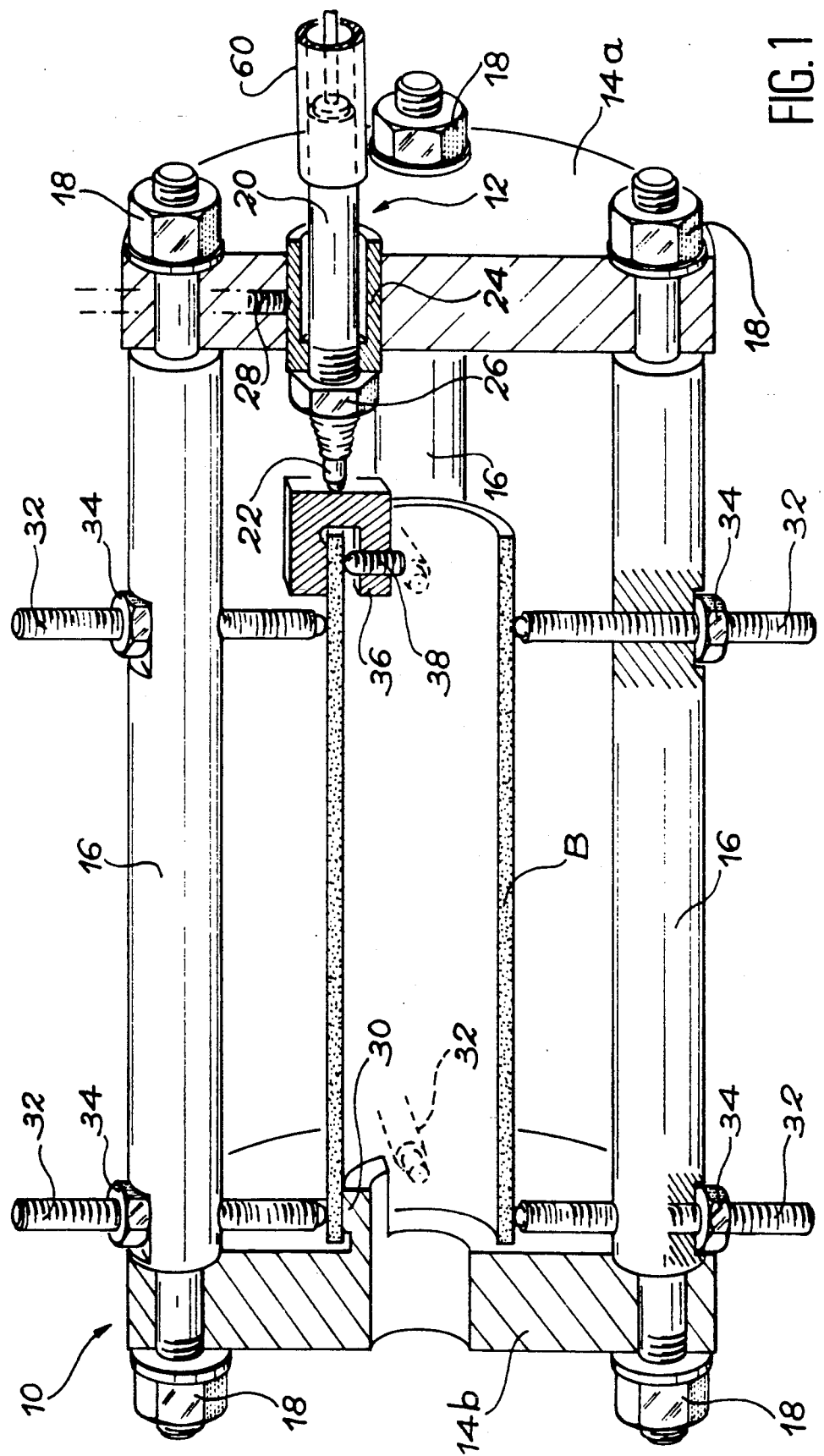
FIG. 1 is a perspective partially cutaway view of a rigid cradle constituting one part of a device used to determine the coefficient of the hydric expansion $\beta$ of a composite structure from a sample of this structure, which in this case has the shape of a tubular bar.

The main elements of this dilatometer are shown on FIG. 1 on which the reference 10 generally denotes a rigid cradle supporting the sample to be tested, the reference 12 denoting a displacement transducer mounted on this rigid cradle.

The rigid cradle 10 includes two solid end plates 14a and 14b forming two parallel and coaxial disks connected at their periphery by four cylindrical regularly spaced braces 16, three of these braces appearing on FIG. 1. The extremities of each of the braces 16 exhibits sections with a smaller diameter and which traverse holes formed in the end plates. Nuts 18 screwed onto the threaded extremities of these smaller diameter sections make it possible to flange-mount the end plates 14a and 14b on the braces 16 so as to form the rigid cradle 10. The end plates 14a and 14b, like the braces 16, are made of a material having a coefficient of thermic expansion as low as possible, such as Invar (registered trade mark).

The displacement transducer 12 is a contact transducer with detection by a linear differential transformer (not shown) housed in a body 20 in which a contact finger 22 is axially guided by means of a roller bearing (not shown). This transducer may be a SCHAEVITZ transducer, model LBB-375-TA-060. This transducer 12 is mounted in the end plate 14a in a position parallel and offset with respect to the axis of the latter within a radial plane containing the axes of two of the braces 16.

The mounting of the transducer 12 in the end plate 14a is effected by means of a ring 24 screwed onto a threading formed on the body 20 of the transducer and blocked by a counternut 26. This ring 24 freely slides in a bore formed in the end plate 14a and it is blocked in the desired position by a screw 28 whose axis is contained in the median plane of the end plate 14a.

On its face turned towards the end plate 14a, the end plate 14b comprises a projecting section 30 which has the shape of an arc of a circle centered on the axis of the end plate 14b and with one generating line of the outer surface being roughly aligned with the axis of the displacement transducer 12.

Immediately close to the end plate 14b and at least another location situated at a certain distance from the end plate 14a, each of the braces 16 is pierced with a tapped hole whose axis is orientated radially with respect to the axis common to the two end plates. Threaded rods 32 are received in these tapped holes and may be rendered immobile by counternuts 34. One of these threaded rods 32, shown at the top on the left on FIG. 1, is found opposite the outer surface of the projecting section 30 and, along with the latter, constitutes a device for clamping one extremity of the sample adjacent to the end plate 14b. The other threaded rods 32 make it possible to keep the sample in the desired position inside the cradle 10, thus avoiding it from buckling, especially when this involves a thin or anisotropic plate.

So as to complete the assembly, an intermediate U-shaped piece 36 is provided so as to be inserted between the extremity of the sample nearest the end plate 14a and the contact finger 22 of the transducer 12. The intermediate piece 36 overlaps the corresponding extremity of the sample and clamps the opposing faces of the latter with the aid of a screw 38 traversing one of the branches formed by this piece.

FIG. 1 more precisely illustrates the case where the sample placed in the rigid cradle 10 is a tubular bar section B. This section is placed in such a way that the projecting section 30 of the end plate 14b penetrates into one of its extremities without the end face of the bar section B being in contact with the end plate 14b. The corresponding extremity of the bar section B is immobilized by clamping against the projecting section 30 with the aid of the threaded rod 32 opposite this section 30.

In addition, the intermediate piece 36 is secured by clamping with the screw to the opposing extremity of the bar section B on the same generating line of this section as the one clamped between the threaded rod 32 and the projecting section 30. Here again, clamping of the piece 36 on the bar section B is effected in such a way that the end face of this section is not in direct contact with the intermediate piece 36.

The particular mounting, described above and in which the bar section B does not take support on its end faces but by clamping on its lateral faces, ensures that the edge effects able to occur on the end faces do not introduce errors in the measurements. In fact, the variation of the rate of humidity in the sample may result in the sample having anisotropic deformations at its end faces.

The positioning and holding of the sample formed by the bar section B inside the rigid cradle 10 are ensured by the threaded rods 32 so that the axis of the bar section is parallel to or merged with the axis common to the end plates 14a and 14b. The contact finger 22 of the displacement transducer 12 is then brought into contact with the intermediate piece by causing the ring 24 to slide in the end plate 14a and then this ring is blocked with the aid of the screw 28. The transducer 12 is then virtually aligned with the generating line of the bar section B, one of its extremities being clamped between the projecting section 30 and the threaded rod 32 opposite it.

Figure 2:
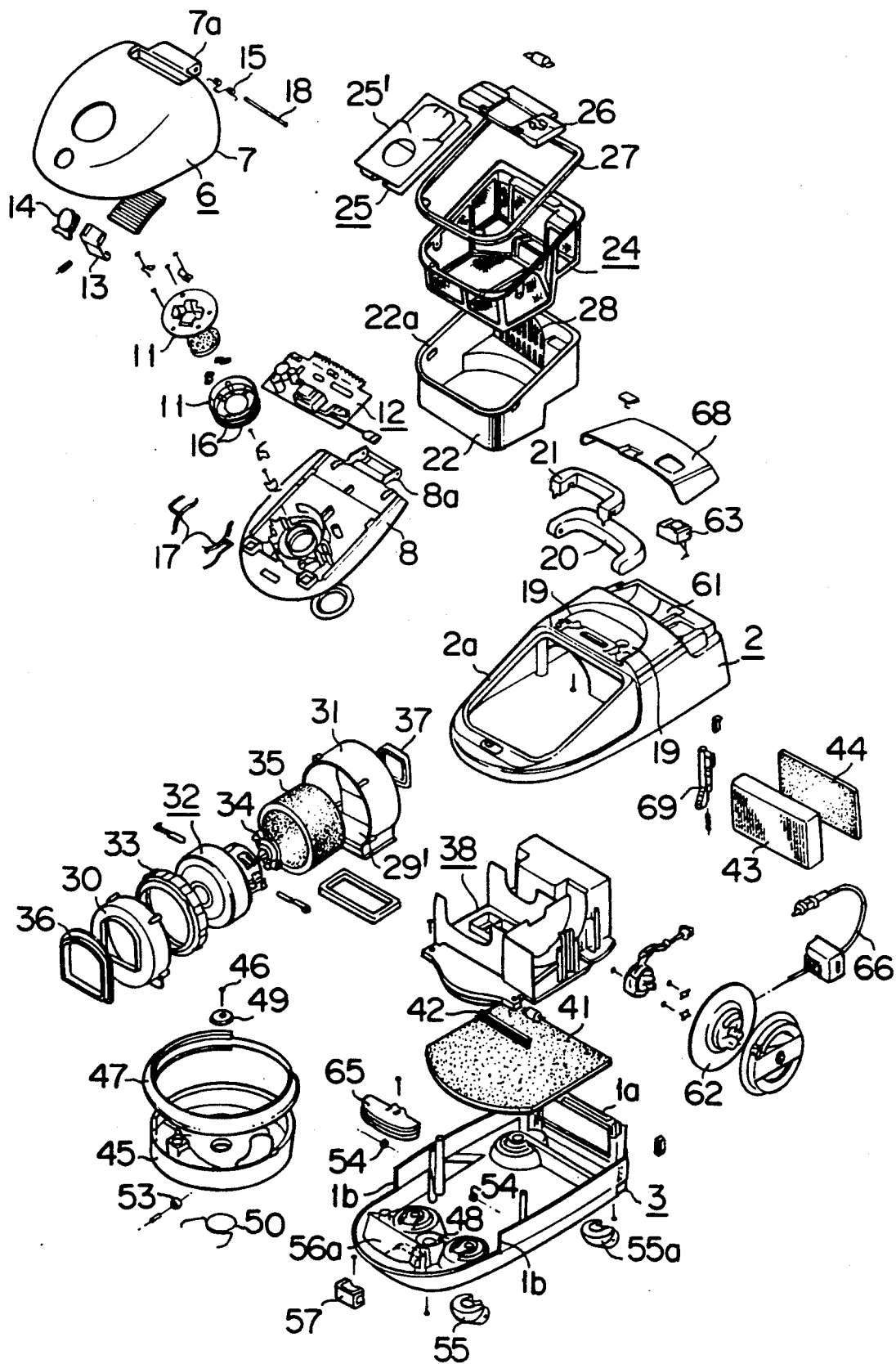

As respectively shown on FIGS. 2 and 3, the assembly is effected similarly when the sample is a section with a honeycombed structure NA and when the sample is a plate section P.

More precisely, when the sample is a honeycombed structure section NA (FIG. 2), one P1 of the lateral plates P1, P2 of this section is placed in the alignment of the axis of the transducer 12, one first extremity of this plate P1 being clamped between the projecting section 30 of the end plate 14b and the threaded rod 32 opposite it, whereas the opposing extremity of this plate P1 is clamped in the intermediate piece 36 by the screw 38.

When the sample is a plate section P (FIG. 3), the mounting is the same as that of the plate P1 of the honeycombed structure section NA.

In addition to the rigid cradle 10 and the displacement transducer 12 associated with this cradle, the device of the invention includes other elements to be described with reference to FIG. 4.

Figure 4:
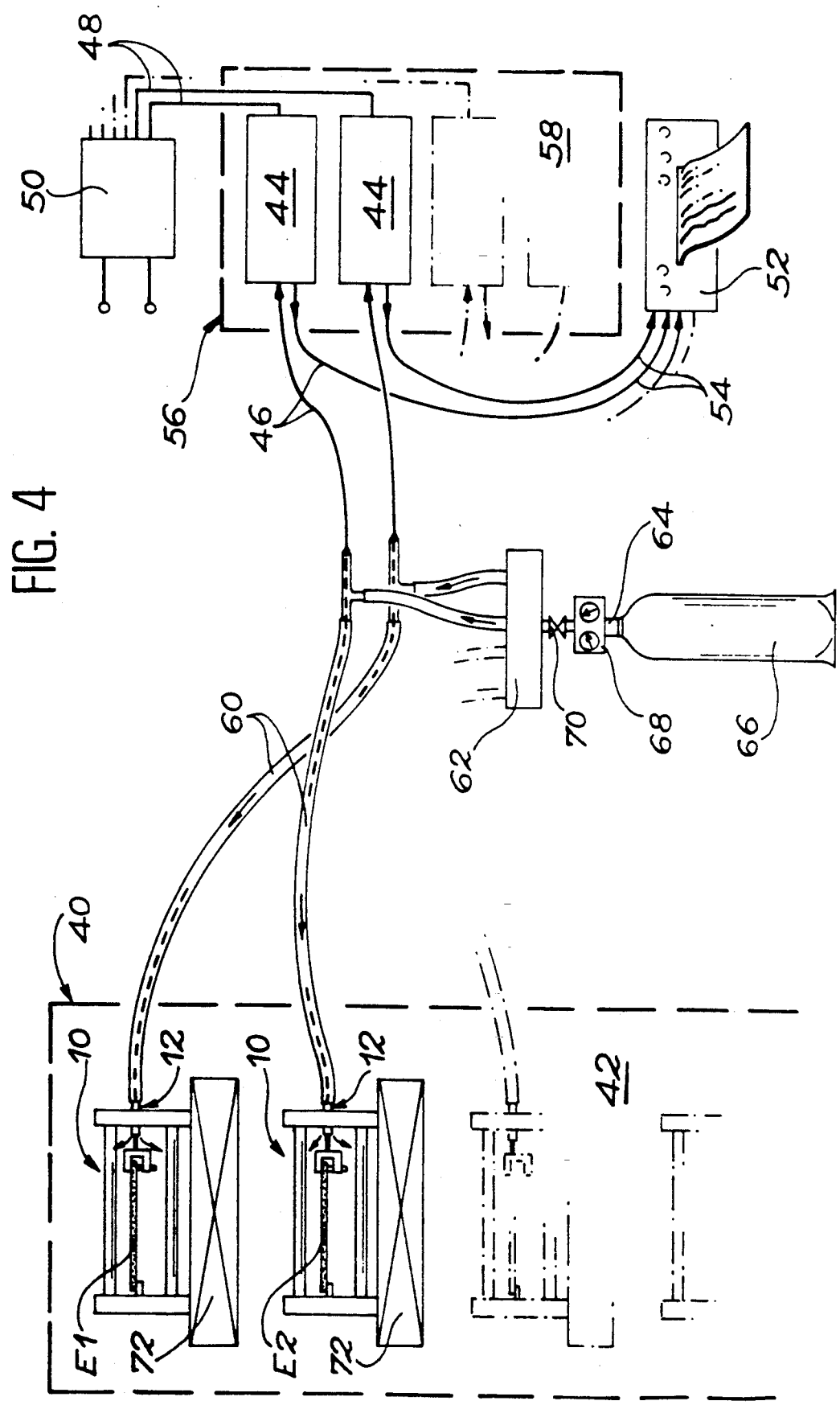
FIG. 4 is a diagrammatic view of a device according to the invention and making it possible to determine the coefficient of the hydric expansion of a composite structure.

FIG. 4 shows that the device advantageously includes several rigid cradles 10 on which samples E1, E2, etc., are mounted, which may be the bar sections B, the honeycombed structure sections NA or the plate sections P, depending on the measurements to be carried out. These rigid cradles 10 are placed in a climatic chamber 40 which makes it possible to control at will the temperature and hygrometry characteristics in the volume 42 delimited by this chamber.

The displacement transducer 12 associated with each of the rigid cradles 10 is electrically connected to a power source 44 by an electric conductor 46. Each power source 44 is itself connected to the mains supply by an electric conductor 48 through a d.c.-a.c. converter 50 making it possible to stabilize the mains voltage to ±3%. The outputs of the power sources 44 are connected to a multichannel recorder 52 or to any equivalent display device by means of electric conductors 54.

So as to improve the accuracy of the measurements carried out, the power sources 44 are preferably placed inside a second climatic chamber 56 whose internal volume 58 is kept at a constant temperature, such as about 22° C.

The installation described above makes it possible to electrically feed the displacement transducers 12 and to display on the recorder 52 the dimensional variations of the samples detected by the various transducers.

According to one main characteristic of the invention, the device further includes means making it possible to continuously keep the displacement transducers 12 in virtually unvarying humidity conditions through the period of the measurements, that is for several weeks. In the absence of these means, the transducers would undergo an amplitude drift comparable to the amplitude of the displacements to be measured, this being explained by the fact that the windings of the differential transformers are embedded in a resin which is sensitive, just like the composite materials to be tested, to humidity variations.

As shown on FIGS. 1 and 4, a flexible pipe 60 is shrunk onto the body 20 of each of the transducers 12 opposite the contact fingers 22. Outside the climatic chamber 40, each of the pipes 60 is connected by a single filter onto a pipe 64 whose opposing extremity is connected to a compressed dry air source, such as a bottle 66. A pressure regulator 68 and a valve 70 are placed on the pipe 64.

This part of the device makes it possible to inject a controlled flow of dry air into each of the displacement transducers 12. The effect of this dry air is to keep the transducers 12 within a humidity range which remains constant despite the humidity variations occuring in the chamber 40. The flowrate of the air injected into the transducers is nevertheless sufficiently small so as to avoid modifying the humidity around the samples E1, E2.

So as to be able to deduce the value of the coefficient of hydric expansion $\beta$ from the deformation measurements carried out by means of the transducers 12, it is necessary to be able to associate with these deformation measurements those measurements indicating the amount of water present in the samples. In order to do this, the weight of the samples is controlled, for example by making a double of each of the samples and by at specific moments taking out the doubles of the samples placed in the cradles so as to weigh them outside the climatic chamber.

These double samples may also be hung from a pair of scales placed above the climatic chamber and whose sample carrier is a wire passing through a hole made in the roof. This disposition enables the weight to be continuously recorded.

In order to carry out a measurement, the samples are mounted in the rigid cradles, as described earlier, and are then placed in a vacuum chamber where they are firstly drained. By monitoring the evolution of the weight of the time-controlled accompanying samples, the samples are known to be dry when this weight is no longer evolving. The devices are then transferred into the climatic chamber 40 and are equipped with the transducers 12. After the temperature of the assembly has stabilized at a desired level, the humidity is progressively admitted as far as the rate agreed. The measurement of the evolution of the length of the samples according to the humidity is then able to be started.

So as to carry out this measurement, the recorder 52 is started, the injection of dry air into the transducers 12 from the bottle 66 being continuously provided for several days and the power sources 56 constantly carrying current.

The temperature inside the chamber 40 is kept constant throughout the measurement, for example at a value close to 70° C., which constitutes a compromise making it possible to accelerate the absorption of the water by the samples without damaging the resin. However, a temperature of less than 70° C. may be chosen.

From this moment, the samples are slowly impregnated with water. As the body of water absorbed is known, for example with the aid of the scales 72, and as the evolution of the length of the samples is displayed on the recorder 52, it is possible to determine the coefficient of the hydric expansion $\beta$ of the samples E1, E2 by applying the equation (1). In one embodiment (not shown), this coefficient may moreover be determined directly by a computer receiving the signals respectively representing the weight and length of the samples.

By means of the invention, which makes it possible to carry out extremely accurate and stable length measurements independently of the ambient humidity, it is thus possible to anticipate the behaviour of composite structures intended, for example, to be used in space applications. In particular, it is possible, during the lifetime of structures supporting embarked optics, to take account of the length evolution of these structures on account of them being drained in a space vacuum. The precisions of current optics may thus be multiplied by about ten.

Of course, the invention is not merely restricted to the embodiment described above by way of example, but covers all its variants. Thus, the structure of the rigid cradle may differ from the one described and any number of cradles may simultaneously be placed in the climatic chamber, provided, however, that the proper operating limits of this chamber are not exceeded.

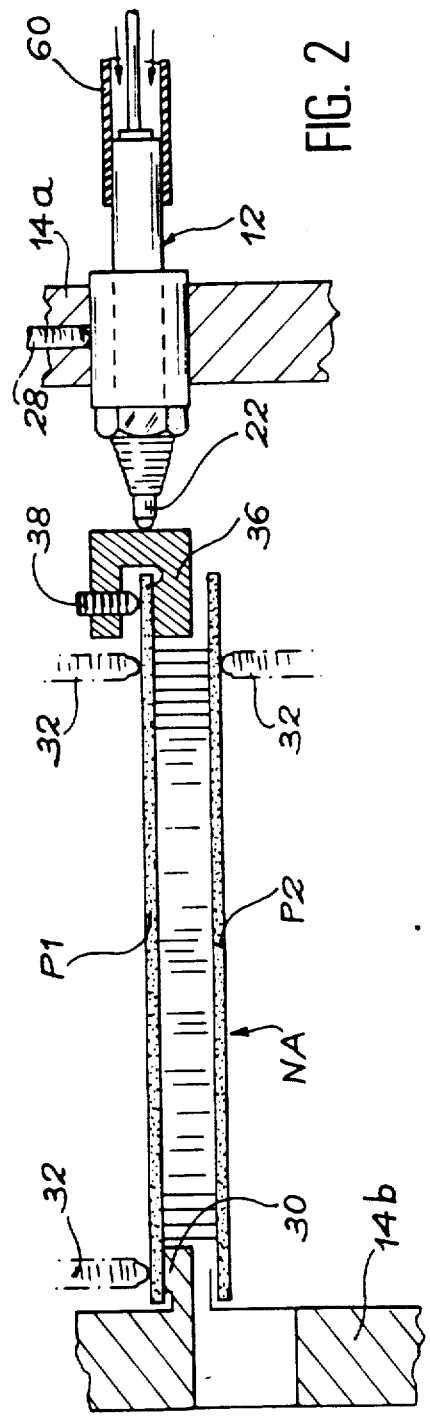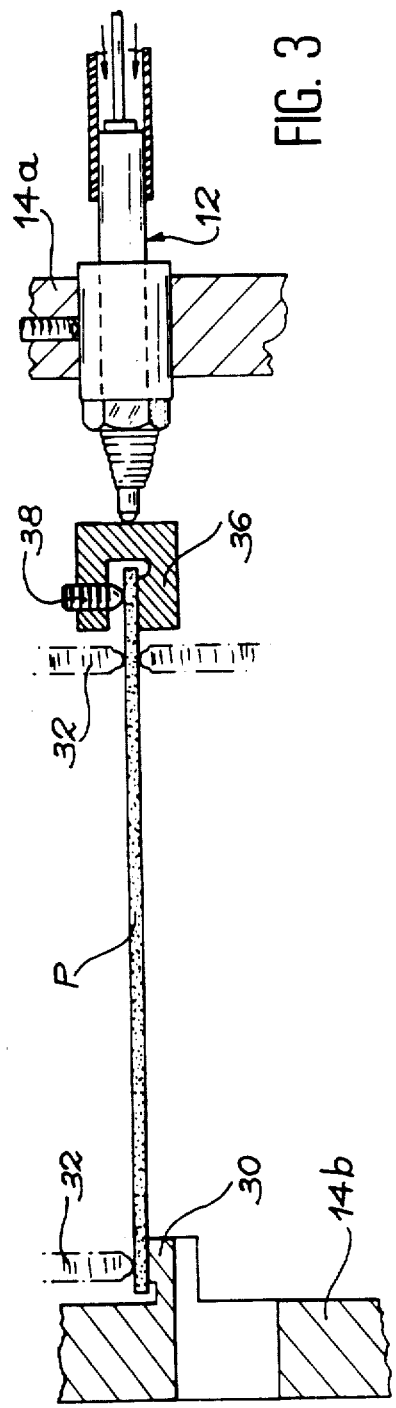

What is claimed is:

1. System making it possible to determine the coefficient of the hydric expansion $\beta$ of the elements of a composite structure and including:
   a rigid cradle made of a thermically stable material and including means to maintain in a desired position a sample of said structure and means to immobilize a first extremity of the sample;
   a displacement transducer mounted on the rigid cradle opposite a second extremity of the sample opposing the first extremity so as to measure the length variations of the sample;
   a tube for admitting dry air into the transducer and connected to a dry air source and having one extremity opposing said source overlapping one rear section of the displacement transducer;
   a climatic chamber for receiving the rigid cradle and its displacement transducer and comprising means to vary the humidity of the atmosphere surrounding the cradle and the transducer within a determined range; and
   means to measure the weight variation of the sample.

2. System according to claim 1, wherein the displacement transducer is a linear differential transformer detection transducer comprising a contact finger axially guided by a roller bearing.

3. System according to claim 2, wherein the means to immobilize the first extremity of the sample are clamping means taking support on the lateral faces of the latter and the contact finger of the transducer is adapted to come into contact with an intermediate member clamped onto the lateral faces of the sample close to the second extremity of the latter.

4. System according to claim 1, wherein the displacement transducer is electrically connected to an electric power device placed in a second chamber at a constant temperature.

5. System according to claim 4, wherein the electric power device is electrically connected to a mains supply by means of a d.c.-a.c. converter stabilizing the voltage.

6. System according to claim 1, wherein the dry air intake tube is connected to the dry air source through a pressure regulator, a flowrate control device and filtering means.

* * * * *

UNITED STATES PATENT AND TRADEMARK OFFICE
CERTIFICATE OF CORRECTION

PATENT NO. : 5,134,891

DATED : August 4, 1992

INVENTOR(S) : Maurice Canevet, et al

Page 1 of 2

It is certified that error appears in the above-identified patent and that said Letters Patent is hereby corrected as shown below:

The drawing sheet, consisting of Fig. 2, should be deleted to be replaced with the drawing sheet, consisting of Figs. 2 and 3, as shown on the attached page.

Signed and Sealed this

Twenty-seventh Day of April, 1993

Attest:

MICHAEL K. KIRK

*Attesting Officer*     Acting Commissioner of Patents and Trademarks